United States Patent
Eldridge et al.

[11] Patent Number: 6,120,539
[45] Date of Patent: Sep. 19, 2000

[54] PROSTHETIC REPAIR FABRIC

[75] Inventors: Stephen N. Eldridge, Cranston, R.I.; Milo A. Titone, Wilmington, Del.

[73] Assignee: C. R. Bard Inc., Murray Hill, N.J.

[21] Appl. No.: 08/850,217

[22] Filed: May 1, 1997

[51] Int. Cl.[7] .................................. A61F 2/02; A61F 2/06; A61F 2/08

[52] U.S. Cl. ..................................... 623/11.11; 623/14.13; 623/902; 606/213; 600/37

[58] Field of Search .................................. 623/11, 12, 13, 623/14, 15, 16

[56] References Cited

U.S. PATENT DOCUMENTS

| | | |
|---|---|---|
| 2,621,145 | 12/1952 | Sano . |
| 2,671,444 | 12/1954 | Pease, Jr. . |
| 3,272,204 | 9/1966 | Artandi et al. . |
| 3,625,209 | 12/1971 | Clark . |
| 3,953,566 | 4/1976 | Gore . |
| 3,965,703 | 6/1976 | Barnhardt . |
| 4,051,848 | 10/1977 | Levine . |
| 4,187,390 | 2/1980 | Gore . |
| 4,277,429 | 7/1981 | Okita . |
| 4,347,847 | 9/1982 | Usher . |
| 4,400,833 | 8/1983 | Kurland . |
| 4,403,604 | 9/1983 | Wilkinson et al. . |
| 4,452,245 | 6/1984 | Usher . |
| 4,478,665 | 10/1984 | Hubis . |
| 4,585,458 | 4/1986 | Kurland . |
| 4,655,221 | 4/1987 | Devereux . |
| 4,713,075 | 12/1987 | Kurland . |
| 4,725,279 | 2/1988 | Woodroof . |
| 4,760,102 | 7/1988 | Moriyama et al. . |
| 4,769,038 | 9/1988 | Bendavid et al. . |
| 4,796,603 | 1/1989 | Dahlke et al. . |
| 4,854,316 | 8/1989 | Davis . |
| 4,871,365 | 10/1989 | Dumican . |
| 4,882,162 | 11/1989 | Ikada et al. . |
| 4,955,907 | 9/1990 | Ledergerber . |
| 4,997,440 | 3/1991 | Dumican . |
| 5,002,551 | 3/1991 | Linsky et al. . |
| 5,092,884 | 3/1992 | Devereux et al. . |

(List continued on next page.)

FOREIGN PATENT DOCUMENTS

| | | |
|---|---|---|
| 2114282 | 7/1994 | Canada . |
| 0 194 172 A1 | 9/1986 | European Pat. Off. . |
| 0 334 046 A2 | 2/1989 | European Pat. Off. . |
| 0 358 819 A1 | 3/1990 | European Pat. Off. . |
| 1 352 282 | 6/1972 | United Kingdom . |
| WO 82/04390 | 12/1982 | WIPO . |
| WO 92/10218 | 6/1992 | WIPO . |
| WO 92/19162 | 11/1992 | WIPO . |
| WO 93 17635 | 9/1993 | WIPO . |
| WO 96/09795 | 4/1996 | WIPO . |

OTHER PUBLICATIONS

Alonzo P. Walker, M.D., James Henderson, D.V.M. and Robert E. Condon, M.D., "Double–Layer Protheses for Repair of Abdominal Wall Defects in a Rabbit Model", pp. 32–37, *Journal of Surgical Research*, vol. 55, No. 1, Jul. 1993.

Brown, G. L., et al., Comparison of Prosthetic Materials for Abdominal Wall Reconstructions in the Presence of Contamination and Infection, Reprinted from Annals of Surgery, vol. 20., No. 6, Jun. 1985.

Jenkins, S.D., et al., A comparison of prothetic materials used to repair abdominal wall defects, Surgery, Aug. 1983.

INTERCEED(TC7) Adhesion Barrier Study Group (Cohen, Stephen M., et al.), Prevention of postsurgical adhesions by INTERCEED9TC7),*an absorbable adhesion barrier: a prospective, randomized multicenter Clinical study, Fertility and Sterility, vol. 51, No. 6, Jun. 1989.

Cardon, M.D., Hernando, "PROSTHOKERATOPLASTY", Cornea, vol. 2, No. 3, 1983.

*Primary Examiner*—Mickey Yu
*Assistant Examiner*—Choon P. Koh
*Attorney, Agent, or Firm*—Wolf, Greenfield & Sacks, P.C.

[57] ABSTRACT

A prosthetic repair fabric including a sheet of tissue infiltratable fabric and a second sheet, also preferably including tissue infiltratable fabric, which is united with the first sheet. The second sheet is fused to an adhesion resistant barrier, forming a laminate composite prosthesis without degrading the mechanical properties or tissue ingrowth capability of the first sheet.

22 Claims, 2 Drawing Sheets

U.S. PATENT DOCUMENTS

| | | |
|---|---|---|
| 5,100,422 | 3/1992 | Berguer et al. . |
| 5,104,400 | 4/1992 | Berguer et al. . |
| 5,110,527 | 5/1992 | Harada . |
| 5,116,360 | 5/1992 | Pinchuk et al. . |
| 5,141,522 | 8/1992 | Landi . |
| 5,147,401 | 9/1992 | Bakker et al. . |
| 5,222,987 | 6/1993 | Jones ........................................ 623/16 |
| 5,234,739 | 8/1993 | Tanaru et al. . |
| 5,234,751 | 8/1993 | Harada . |
| 5,254,133 | 10/1993 | Seid . |
| 5,258,000 | 11/1993 | Gianturco . |
| 5,282,851 | 2/1994 | Jacob-LaBarre . |
| 5,292,328 | 3/1994 | Hain et al. . |
| 5,326,355 | 7/1994 | Landi . |
| 5,433,996 | 7/1995 | Kranzler et al. . |
| 5,461,885 | 10/1995 | Yokoyama et al. . |
| 5,480,436 | 1/1996 | Bakker et al. . |
| 5,508,036 | 4/1996 | Bakker et al. . |
| 5,569,273 | 10/1996 | Titone et al. ............................ 623/11 |
| 5,593,441 | 1/1997 | Lichtenstein et al. .................... 623/66 |
| 5,614,284 | 3/1997 | Kranzler et al. ......................... 623/11 |
| 5,695,525 | 12/1997 | Mulhauser et al. . |
| 5,716,409 | 2/1998 | Debbas .................................... 623/13 |
| 5,725,577 | 3/1998 | Saxon ...................................... 623/11 |
| 5,733,337 | 3/1998 | Carr, Jr. et al. ........................... 623/12 |
| 5,743,917 | 4/1998 | Saxon . |
| 5,766,246 | 6/1998 | Mulhauser et al. ...................... 623/11 |

PROSTHETIC REPAIR FABRIC

FIELD OF INVENTION

The present invention relates to a prosthetic repair fabric and, more particularly, to an adhesion resistant, dual layer knitted fabric for use in soft tissue repair and reconstruction.

BACKGROUND OF THE INVENTION

Various prosthetic repair materials have been proposed for mending inguinal hernias and for reconstructing the abdominal and chest wall. MARLEX mesh, a single bar warp knit, dual course Atlas polypropylene monofilament fabric, is exemplary of an implant material that has been successfully used in soft tissue reinforcement and defect closure.

A concern had been raised that MARLEX mesh may form postoperative adhesions with the abdominal viscera, such as the intestines, when used in the repair of inguinal hernias and other abdominal wall defects. Similarly, there was a suggestion that intra-thoracic viscera (i.e. heart and lungs) could adhere to the porous prosthetic repair material after chest wall reconstruction. To alleviate these concerns, it had been proposed in U.S. Pat. No. 5,593,441, assigned to C. R. Bard, Inc., also the assignee of the present application, to cover the MARLEX fabric (or other tissue infiltratable material) with an adhesion resistant barrier, such as a sheet of expanded PTFE. The composite prosthesis is surgically placed so that the barrier isolates the sensitive viscera from the porous fabric, preventing the formation of postoperative adhesions.

One method of forming the composite is to laminate the mesh and adhesion resistant cover together. Preliminary investigation, however, suggests that fusing a sheet of MARLEX to a barrier layer of ePTFE may detrimentally affect the tissue infiltratability of the prosthesis. With one surface of the porous fabric covered by the ePTFE, the ingrowing tissue may be unable to completely incorporate the mesh.

Accordingly, there is a need for an improved laminate prosthesis for the repair of tissue or muscle wall defects that exhibits acceptable tissue ingrowth properties.

SUMMARY OF THE INVENTION

The present invention is a prosthetic repair fabric for reinforcing or repairing a damaged muscle or tissue wall and includes a first sheet of porous and tissue infiltratable material, an adhesion resistant, microporous barrier sheet for isolating the first sheet from sensitive tissue and organs after implantation, and a second sheet that is united with the porous and tissue infiltratable first sheet and which also is fused to the barrier sheet to form a laminate composite construction. Preferably, the second sheet also is porous and tissue infiltratable and at least a surface portion of the lower melting temperature porous second sheet melts during lamination and flows into the microporous structure of the adhesion resistant covering, encapsulating the void network of the barrier upon solidification to form a strong mechanical fixation between the two materials. Degradation of physical properties of the composite implant is avoided since only one of the fabric sheets, the fabric panel adjacent the barrier, is melted during assembly of the prosthesis, allowing the other porous panel to retain its full tissue ingrowth potential and strength.

In one embodiment, the laminate includes two united sheets of warp knitted polypropylene monofilament, preferably having a 2 course Atlas pattern, that are bonded to a sheet of submicron porous expanded PTFE. The two tissue ingrowth panels may be simultaneously knitted on a double needle bed machine and then joined together by intermittent or continuous machine direction, but laterally spaced, stitches. Where the stitches are intermittent, the connecting yarn may be laid in between the fabric panels. Preferably, the sheets are knitted together as the panels are formed on the knitting machine. Alternatively, the dual layers may be tacked together after the fabric panels have been removed from the knitting device. The dual layer, porous polypropylene fabric is laminated to the sheet of expanded PTFE by a combination of heat and pressure. The top mesh layer becomes fused to the expanded PTFE while the lower mesh layer, which is not melted, retains its shape and physical characteristics.

Another important embodiment of the invention involves a method of limiting the incidence of postoperative adhesions arising from the repair of an opening in a tissue or muscle wall. The method includes the steps of providing a composite prosthesis including first and second sheets of tissue infiltratable fabric and an adhesion resistant barrier sheet that is fused to the first fabric sheet, and then positioning the composite prosthesis with the second tissue infiltratable fabric sheet filling or covering, thereby occluding, the tissue or muscle wall opening and with the barrier sheet facing away from the tissue or muscle wall opening and extending between a region of potential postoperative adhesion and the porous fabric sheets. The method has particular applicability in the repair of ventral hernias and in the reconstruction of the chest wall.

In another important embodiment, a dual layer implantable fabric is provided including a pair of warp knit sheets having interstices constructed and arranged for tissue ingrowth so that the fabric becomes secured in place after implantation, wherein the two sheets are united by intermittent stitches of a connecting yarn that is laid in between the intermittent stitches.

It is a general object of the invention to provide a laminated adhesion resistant, composite prosthesis.

Other objects and features of the present invention will become apparent from the following detailed description when taken in connection with the accompanying drawings. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENT

Figure 1:
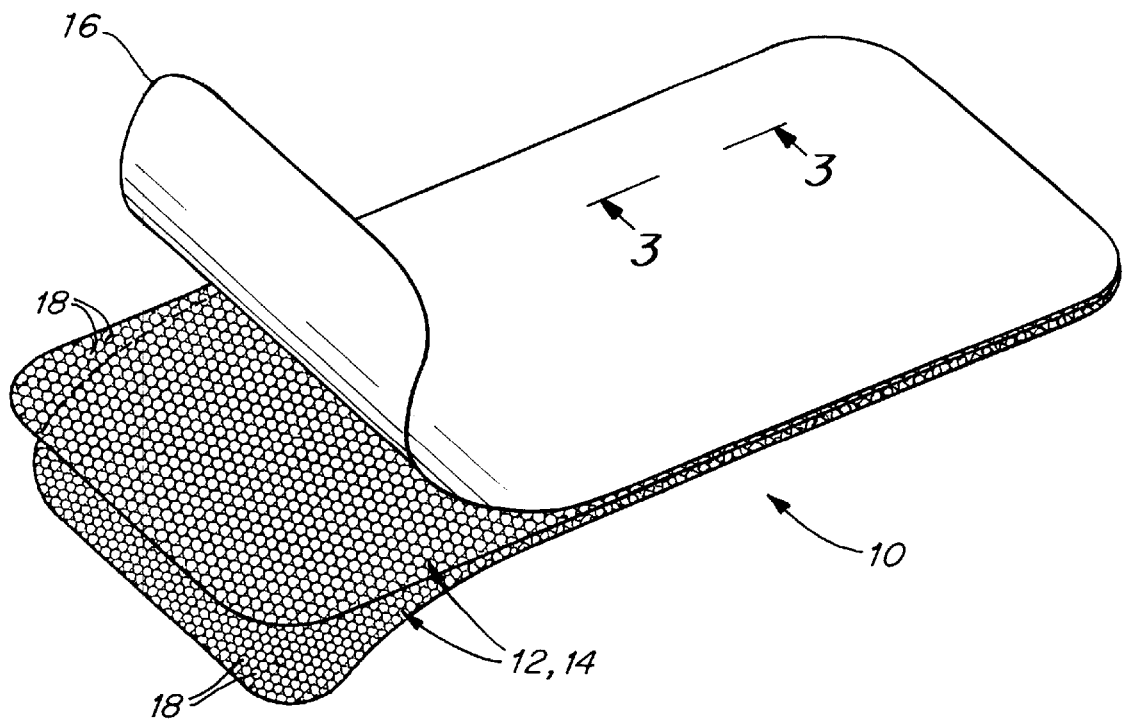
FIG. 1 is an illustration of two knitted layers and ePTFE covering of a prosthetic repair fabric according to the present invention.
Figure 3:
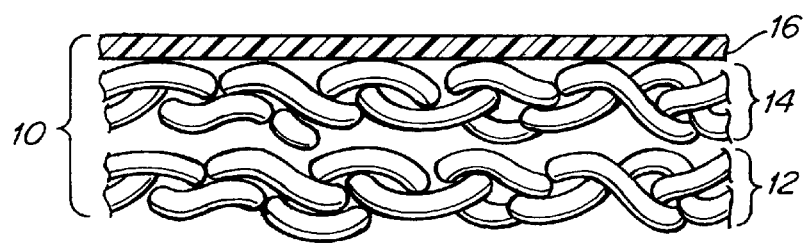
FIG. 3 is an enlarged cross-sectional view taken along section line 3—3 of FIG. 1.

The present invention, illustrated in FIGS. 1 and 3 is a prosthetic repair fabric 10 for reinforcing and closing soft tissue defects, and is particularly indicated for chest wall reconstruction and the repair of ventral hernias. The implant fabric is formed of a biologically compatible, flexible and strong implantable material. The porous character of the fabric allows tissue infiltration to incorporate the prosthetic after implantation. The fabric is sufficiently strong to prevent pullout of anchoring sutures, if utilized during the surgical procedure. The flexible fabric may be collapsed into a slender configuration, such as a roll, which can be supported in, and advanced through, a narrow laparoscopic cannula.

When knitted from polypropylene monofilament yarns, the porous prosthetic repair fabric allows a prompt fibroblastic response through the interstices of the material, forming a secure fibrous/prosthetic layer. The polypropylene monofilament fabric is inert in the presence of infection, non-wettable and has a low foreign body reaction. Other biologically compatible synthetic and natural fabrics which are suitable for tissue reinforcement and defect closure, whether formed of monofilament or multifilament yarns, also are contemplated for application in the dual layer fabric including, without limitation, PROLENE, SOFT TISSUE PATCH (porous ePTFE), SURGIPRO, TRELEX, ATRIUM and MERSELENE.

Each panel 12, 14 of the dual layer fabric preferably has a warp knit single bar, two course Atlas construction, such as is employed in MARLEX mesh. Other knit patterns that are suitable for mending soft tissue defects and for chest and abdominal wall reconstruction also may be employed. In the illustrative embodiment, both the first and second panels are porous and the same knit pattern is employed for both panels. However, the invention contemplates arranging the first and second sheets with different knit patterns. Where the knitted panels have the same construction, the sheets are preferably arranged in mirror image relationship relative to one another; that is, the orientation of the panels is reversed so that the front face of each panel is exposed outwardly while the back faces are internally opposed relative to one another. The two sheets also may be joined together with the first and second panels arranged in the same orientation so that a front face is exposed on the first panel, a back face exposed on the second panel, and back and front faces of the respective sheets opposing each other internally.

The fabric sheets are united together and, preferably, the points of attachment are arranged in the machine direction with lateral spacing between columns of connecting stitches. Stitch spacing ensures physical separation of the opposed panels between the points of attachment. The distance between columns of connecting stitches may by selected to minimize the size of unconnected layers if the fabric is cut during manufacturing or at the time of surgical placement, and an especially preferred spacing is 0.125 inches. Preferably, intermittent chain stitches are employed with the connecting yarn then laid in until the uniting pattern is repeated. The laid-in construction retains the connecting yarn completely within the fabric. Although an intermittent chain stitch is preferred, a continuous chain stitch also may be employed. Other stitching arrangements for joining the panels together also are contemplated as would be apparent to one of skill in the art. Other mechanisms for connecting two layers of fabric, such as tacking, stapling, heat bonding, chemical bonding, to name but a few, also are within the scope of the invention so long as the rendered fabric provides the desired performance characteristics.

The dual layer fabric is covered with a barrier material 16 that does not substantially stimulate adhesion formation when implanted in tissue. The barrier isolates the porous fabric from sensitive tissues and organs that may come in contact with the prosthesis, limiting the incidence of postoperative adhesions. The barrier sheet may be formed of expanded polytetrafluoroethylene (ePTFE) having a fine pore size that discourages tissue ingrowth and viscera adhesion. A representative and non-limiting sampling of other suitable barrier materials includes silicone elastomer and microporous polypropylene. Autogenous, heterogenous and xenogeneic tissue also are contemplated including, for example, pericardium and small intestine submucosa.

Because the composite includes a first knit sheet 12 and then a second sheet 14 rather than a single knit layer, the barrier material 16 may be fused to the second sheet without degrading the physical characteristics of the first knit panel. Consequently, the unfused layer will remain mechanically strong after formation of the composite and, since the interstices 18 in the unfused layer 12 remain open, tissue ingrowth should not be adversely affected. In a preferred embodiment, the barrier and the knitted fabric are fused at substantially all points of contact, even though one or both connecting surfaces may be uneven and irregular. Such complete bonding prevents peel back of the barrier sheet after implantation which, otherwise, could lead to postoperative adhesions. Although it is preferred to employ a pair of knit sheets as the two components of the dual layer fabric, a non-porous second sheet may alternatively be employed to fuse a first tissue infiltratable sheet to the barrier.

Figure 2:
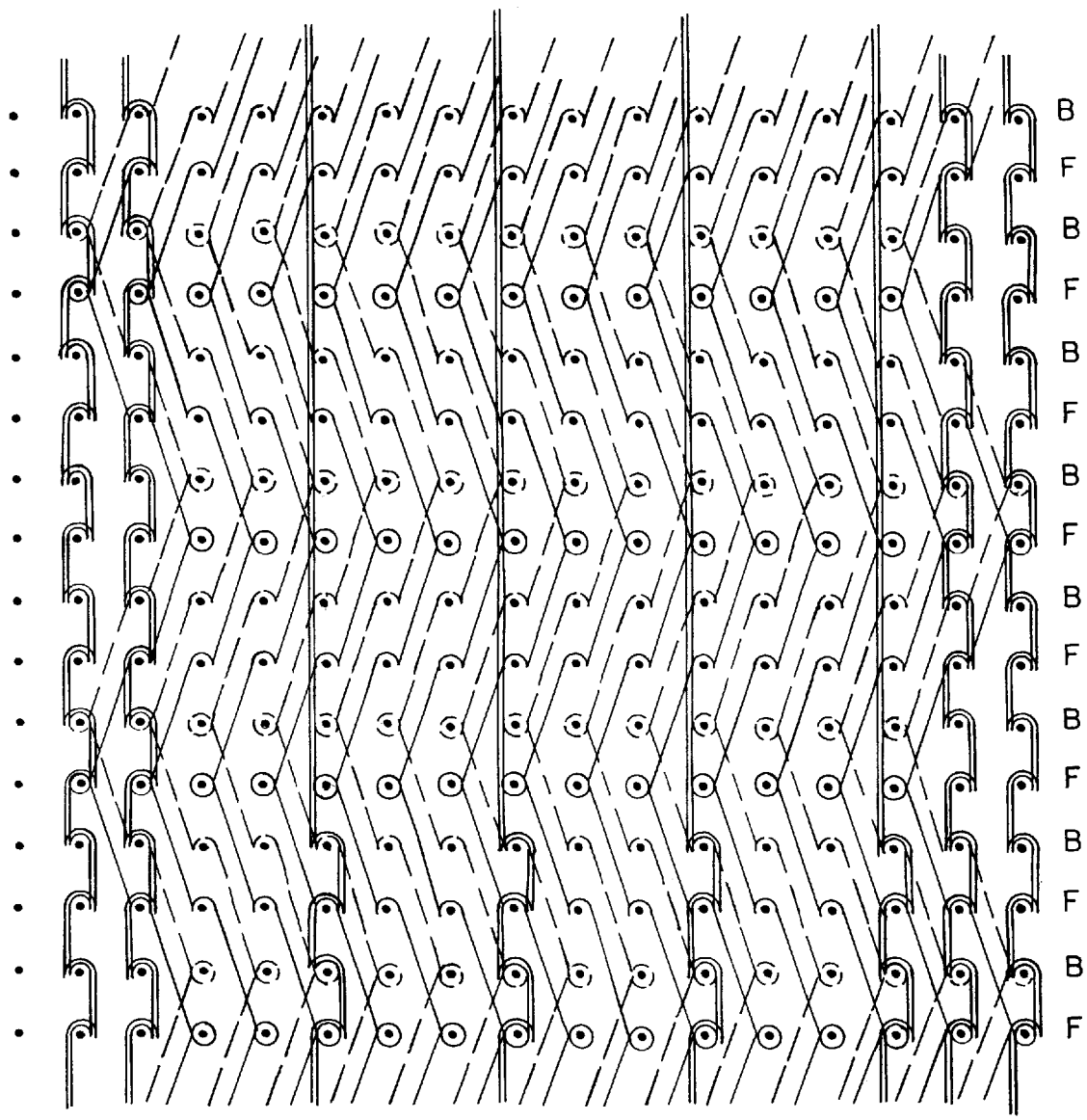
FIG. 2 is a chain lapping pattern for a preferred embodiment of the prosthetic repair fabric.

A representative procedure for forming a dual layer fabric according to the present invention will now be described. In this example, both panels are porous and have a 2 course Atlas construction (MARLEX mesh). The fabric is warp knitted from 0.006 inch diameter polypropylene monofilament on a fully threaded, double needle bar machine (Kiddie DE14 Rachel), stitching on every needle and traversing across three needles. Fabric parameters, such as quality, stretch, and yarn size may vary depending upon the application. The panels are knit simultaneously but independently, with the first panel being knit on the front needle bed and the second panel being knit on the second needle bed. Connecting stitches, such as one or more chain stitches, are intermittently knit needle bed to needle bed in a predetermined spacing pattern, uniting the separately knitted sheets together. The connecting yarn is then laid-in between the front and back panels until the chain stitch pattern repeats itself. In the chain pattern illustrated in FIG. 1, every third guide (one in two out) is threaded with the connecting yarn and the pair of chain stitches are spaced every 15 courses. A selvedge edge on each side of the warp knit fabric is provided by continuously chain stitching bed to bed the outermost two needles of each machine edge of the fabric. The guide pattern for the two course Atlas construction illustrated in FIG. 2 is 2-0 2-4 4-6 4-2, with a dwell pattern on the opposite needle bed of 2-2 4-4 4-4 2-2. The chain stitch guide pattern and the selvedge guide pattern are 0-2 2-0. Other selvedge and connecting stitch patterns and spacing may be employed as would be apparent to one of skill in the art.

A barrier sheet of ePTFE may be laminated or fused to one of the two knit panels by the combination of heat and pressure, forming an adhesion resistant composite implant. The warp knit dual layer fabric is placed on a depressurized air bladder and then is covered by the ePTFE sheet. A steel platen, pre-heated to 350–400° F., is applied against the ePTFE sheet at the same time the bladder is pressurized between 2–10 psi for a brief period of time (1–8 seconds). The inflated bladder subjects the varyingly thick, or irregularly contoured, double panel fabric to a uniform pressure distribution. At least a surface portion of the top knit panel melts and becomes encapsulated in the submicron porous network of the expanded PTFE sheet, mechanically fixing the dual layer fabric and the barrier cover. The lower knit layer does not thermally degrade during the lamination process.

The composite implant which is rendered includes a partially transformed or remelted first knit layer firmly attached to an ePTFE barrier sheet and an essentially unchanged second knit layer with superior strength and tissue ingrowth capability. The warp knit dual layer, polypropylene monofilament mesh fabric has a thickness of approximately 0.060 inches. The ePTFE sheet has a thickness of approximately 0.0035 inches. The overall thickness of the implant is approximately 0.0635 inches.

EXAMPLES

The following examples are illustrative only and are not intended to limit the scope of the present invention.

Physical and performance characteristics were tested including pore size, surface roughness, suture retention strength, and burst strength. Testing methodology and results appear below. In vivo testing protocol and observations also follow.

Pore Size

A Digital Instruments Nanoscope III with a Stand Alone Atomic Force Microscope (AFM) was used in tapping mode to analyze the samples. A silicon probe with a 10 micron probe tip height, 40 degree apex angle, and a tip radius of about 50 Angstroms was used. Resolution was about 1 nanometer. A 10×10 micron area on each sample was scanned. Composite samples were scanned on and off bond sites. Micrographs showing surface topography were obtained for each sample. After the scan was obtained a computer analysis (Grain Size Analysis) was done in which the image was inverted, the height threshold was set, and the average grain size was calculated. A height threshold value of 0.160 microns was determined previously and used for all materials. The height threshold established the depth of penetration into the material surface. The average grain size area was converted to the equivalent round pore diameter in microns by Area=pi $(d/2)^2$ where d=diameter. All pores within the 10 micron scan were analyzed and the number of pores comprising the mean value ranged from 6–100 for each sample.

Surface Roughness

The same 10 micron scan obtained for the pore size analysis was analyzed for surface roughness. The computer calculated the mean roughness (Ra) in microns for the 10 micron scan using the following formula:

$$Ra = (1/L_xL_y)\int_0^{L_y}\int_0^{L_x} |f(x, y)|\,dx\,dy$$

where Lx and Ly are dimensions on the surface and f(x,y) is the surface relative to the center plane. The center plane is a flat plane which intersects the surface such that the surface data bounded by the surface has an equal volume above and below that flat plane.

Suture Retention Strength

A suture of size 3-0 or greater was placed 3–4 mm from the edge of the sample using a small needle. The sample was clamped in the lower jaw and the free ends of the looped suture were clamped in the upper jaw of a tensile testing machine (MTS Corp.) The suture was pulled out of the sample at a rate of 5" per minute with an initial jaw separation of 2.0"–2.5". The peak force required to pull out the suture was recorded. The composite prosthesis was tested in two perpendicular directions and the direction of the lowest strength was reported. The GORE-TEX sample was tested in one direction since it has no directionality.

Burst Strength

A 3" diameter circular piece of material was clamped in the fixture of a standard Mullen Burst tester. Hydraulic pressure was slowly increased causing a rubber diaphragm to inflate and burst the sample. The peak pressure (psi) required to burst the sample was recorded.

In-Vivo Testing

Fifteen 6-month old male Yucatan micro-pigs were randomly assigned to 3 groups of 5 each (28, 84, and 168 day implant groups). 6 hernia repair mesh patches of approximately 4 cm×5 cm in size (2 composite prostheses, 2 GORE-TEX, and 2 MARLEX mesh) were surgically implanted in each animal. There were 10 patches of each material at each time point. The patches were used to repair 6 full-thickness abdominal wall defects arranged in two para-lumbar rows on either side of the midline. The materials were assigned to sites following a rotating sequence. A 20 cm long incision was made down to the peritoneum. Approximately 1.5 cm on either side of the incision, subcutaneous tissue was removed down to the peritoneum. Three 3 cm×4 cm defects were made in the peritoneum. The patches were sewn to the peritoneum and muscle using 12 mattress sutures with 3-0 braided Nylon sutures. The edges of the patches and the abdominal wall were everted away from the abdominal cavity to prevent bowel contact with the suture line and edges of the patches. The skin was closed over the site. The procedure was repeated on the other side of the midline. Five animals were sacrificed at each of 28, 84, and 168 days. Any adhesions to the peritoneal cavity side of the patches were categorized as to organ type and sized by caliper measurement. A tenacity score of 1–3 was assigned to each adhesion (1=easily freed with blunt dissection, 2=difficult to free with blunt dissection, 3=freed with sharp dissection). The tissue ingrowth area into the abdominal wall side of the patches was qualitatively determined by dissection and assigned a score of 1–3 for tenacity as described above.

TABLE 1

Summary of Bench Data (mean ± 1 standard deviation)

| | Composite | | | |
| --- | --- | --- | --- | --- |
| | On Bond | Off Bond | Gore-Tex | Marlex |
| ePTFE Surface Pore Size (microns) (n = 8) | 0.74 ± 0.30 | 0.87 ± 0.49 | 0.19 ± 0.05 | Not Tested |
| ePTFE Surface Roughness (microns) (n = 8) | 0.18 ± 0.03 | 0.20 ± 0.04 | 0.07 ± 0.02 | Not Tested |
| Suture Retention Strength (lbs) (n = 17) | 5.9 ± 1.7 | | 9.2 ± 1.6 | 5.3 ± 0.8 |
| Burst Strength (psi) (n = 17) | 191 ± 9 | | 204 ± 24 | 162 ± 10 |

TABLE 2

Summary of In vivo Data: Percent of Patch Area Covered with Adhesions (mean ± standard deviation)

|  | 28 Day Implants | | | 84 Day Implants | | |
| --- | --- | --- | --- | --- | --- | --- |
|  | Composite | Gore-Tex | Marlex | Composite | Gore-Tex | Marlex |
| Intestinal Adhesions | 2.7 ± 6.7 | 9.8 ± 21.1 | 14.8 ± 18.8 | 0.0 ± 0.0 | 0.0 ± 0.0 | 5.1 ± 15.3 |
| Omental Adhesions | 46.6 ± 49.3 | 40.2 ± 44.4 | 38.6 ± 45.8 | 28.1 ± 36.8 | 4.7 ± 10.9 | 27.1 ± 34.5 |

TABLE 3

Summary of In vivo Data: Percent of Patches with Adhesions

|  | 28 Day Implants | | | 84 Day Implants | | |
| --- | --- | --- | --- | --- | --- | --- |
|  | Comp n = 10 | Gore | Marlex | Comp n = 10 | Gore | Marlex |
| Intestinal Adhesions | 20 | 20 | 50 | 0 | 0 | 20 |
| Omental Adhesions | 60 | 60 | 60 | 50 | 20 | 60 |

|  | Pooled Data | | |
| --- | --- | --- | --- |
|  | Comp n = 20 | Gore | Marlex |
| Intestinal Adhesions | 10 | 10 | 35 |
| Omental Adhesions | 55 | 40 | 60 |

It should be understood that the foregoing description of the invention is intended merely to be illustrative thereof and that other embodiments, modifications, and equivalents of the invention are within the scope of the invention recited in the claims appended hereto.

What is claimed is:

1. A prosthetic repair fabric, comprising:
   a dual layer, biologically compatible and implantable fabric including a first porous knit sheet with interstices constructed and arranged for tissue infiltration and which is susceptible to the formation of adhesions with sensitive tissue and organs and a second sheet that is joined directly to said first sheet; and
   a barrier sheet that is resistant to the formation of adhesions with sensitive tissue and organs and which is overlaid and in contact with said second sheet, wherein at least a surface portion of said second sheet adjacent said barrier is fused to said barrier without degrading the physical characteristics of said first sheet.

2. The prosthetic repair fabric recited in claim 1 wherein said second sheet is a porous knit sheet.

3. The prosthetic repair fabric recited in claim 2 wherein said porous second sheet has a single bar warp knit, dual course Atlas construction.

4. The prosthetic repair fabric recited in claim 1 wherein said first porous knit sheet is formed from polypropylene.

5. The prosthetic repair fabric recited in claim 4 wherein said second sheet is formed from polypropylene.

6. The prosthetic repair fabric recited in claim 1 wherein said barrier sheet is formed from ePTFE.

7. The prosthetic repair fabric of claim 1 wherein at least a portion of said second sheet adjacent said first sheet also includes interstices constructed and arranged for tissue infiltration, wherein said interstices in said portion of said second sheet adjacent said first sheet are not occluded by fusion of said at least surface portion to said barrier sheet so as not to adversely affect tissue ingrowth thereto.

8. The prosthetic repair fabric of claim 1 wherein said first and second sheets are joined by a plurality of points of attachment therebetween, said plurality of points of attachment being spaced from each other so that said first and second sheets are unattached and physically separable from each other between said plurality of points of attachment.

9. The prosthetic repair fabric recited in claim 2, wherein at least one of said first and second porous sheets has a single bar warp knit, dual course Atlas construction.

10. The prosthetic repair fabric recited in claim 9 wherein both of said first and second porous sheets has a single bar warp knit, dual course Atlas construction.

11. The prosthetic repair fabric recited in claim 1, wherein at least one of said first porous sheet and said second sheet is formed of polypropylene.

12. The prosthetic repair fabric according to claim 1, wherein said first sheet is joined to said second sheet with a plurality of stitches of a connecting yarn.

13. The prosthetic repair fabric according to claim 12, wherein said stitches include continuous stitches.

14. The prosthetic repair fabric according to claim 12, wherein said stitches include intermittent stitches.

15. The prosthetic repair fabric according to claim 14, wherein said connecting yarn is laid in between said intermittent stitches.

16. The prosthetic repair fabric according to claim 15, wherein said intermittent stitches are chain stitches.

17. The prosthetic repair fabric according to claim 1, consisting essentially of said first and second sheets and said barrier sheet.

18. The prosthetic repair fabric according to claim 1, wherein said surface portion of said second sheet is fused to said barrier without occluding the interstices in said first sheet so as not to adversely affect tissue ingrowth thereto.

19. The prosthetic repair fabric according to claim 1, wherein said barrier is in contact with said second sheet at a plurality of points.

20. The prosthetic repair fabric of claim 19 wherein said second sheet and said barrier are fused together at all of said plurality of points of contact therebetween.

21. The prosthetic repair fabric according to claim 2, wherein said first sheet is knitted to said second sheet.

22. A method of limiting the incidence of postoperative adhesions arising from the repair of an opening in a tissue or muscle wall, wherein the opening is located near a region of potential postoperative adhesions, comprising the steps of:

provided a composite prosthesis including a first sheet that is tissue infiltratible, a second sheet joined directly to the first sheet, and an adhesion resistant barrier sheet that is fused to the second sheet without degrading the physical and tissue infiltratible characteristics of the first sheet; and positioning the composite prosthesis with the barrier sheet extending between a region of potential postoperative adhesion and the first sheet.

* * * * *